(12) United States Patent
Lo et al.

(10) Patent No.: US 8,293,777 B2
(45) Date of Patent: Oct. 23, 2012

(54) ANGIOTENSIN II RECEPTOR ANTAGONISTS

(75) Inventors: Michael Man-Chu Lo, Edison, NJ (US); Amjad Ali, Freehold, NJ (US); Ravi P. Nargund, East Brunswick, NJ (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 123 days.

(21) Appl. No.: 12/629,419

(22) Filed: Dec. 2, 2009

(65) Prior Publication Data
US 2010/0144810 A1 Jun. 10, 2010

Related U.S. Application Data

(60) Provisional application No. 61/200,964, filed on Dec. 5, 2008.

(51) Int. Cl.
A61K 31/34 (2006.01)
A61K 31/41 (2006.01)
C07D 249/00 (2006.01)
C07D 409/02 (2006.01)

(52) U.S. Cl. ..... 514/383; 514/469; 548/253; 548/306.4; 548/311.1

(58) Field of Classification Search ............... 548/253, 548/306.4, 311.1
See application file for complete search history.

(56) References Cited

FOREIGN PATENT DOCUMENTS
| WO | WO-2005-011646 | * | 2/2005 |
| WO | WO 2005/011646 A2 | | 2/2005 |
| WO | WO 2008/076246 A2 | | 6/2008 |

OTHER PUBLICATIONS

BPAI Decision, Appeal 2011-003949, U.S. Appl. No. 10/566,292, entire document, date: Jul. 27, 2011.*
European Patent Office Search Report for PCT/US2009/066041; Completed Feb. 18, 2010; by authorised officer Stefano Fanni.
Valsartan vs. Other Angiotensin II Receptor Blockers in the Treatment of Hypertension: A Meta-Analytical Approach; R.M. Nixon, et al.,; Journal compilation—Int J Clin Pract, May 2009; pp. 63, 5, 766-775.

* cited by examiner

Primary Examiner — Susannah Chung
(74) Attorney, Agent, or Firm — Richard S. Parr; Catherine D. Fitch

(57) ABSTRACT

A compound having the structure

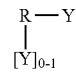

wherein R is an angiotensin receptor antagonist active group, and Y is
Y is selected from the group consisting of

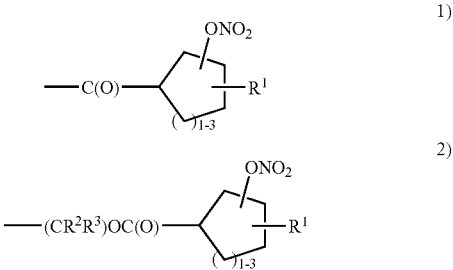

$R^1$ is selected from the group consisting of
—O—$C_{1-6}$ alkyl,
—O-aryl,
—O-heteroaryl,
—O—$C_{3-8}$ cycloalkyl,
—$C_{1-6}$ alkyl,
-aryl,
-heteroaryl, and
—$C_{3-8}$ cycloalkyl;
$R^2$ and $R^3$ are independently selected from the group consisting of hydrogen and $C_{1-4}$ alkyl, or a pharmaceutically acceptable salt or hydrate thereof, which is useful for treating hypertension.

3 Claims, No Drawings

ANGIOTENSIN II RECEPTOR ANTAGONISTS

PRIORITY CLAIM

This application claims the benefit of U.S. Provisional Application No. 61/200,964, filed Dec. 5, 2008.

JOINT RESEARCH AGREEMENT

The claimed invention was made as a result of activities undertaken within the scope of a joint research agreement between Merck & Co., Inc. and NicOx SA. The agreement was executed on Mar. 20, 2006.

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

WO2005011646 describes angiotensin II receptor blocker nitroderivatives, pharmaceutical compositions containing them and their use for the treatment of cardiovascular, renal and chronic liver diseases, inflammatory processes and metabolic syndromes. The publication describes a variety of angiotensin receptor blocker compounds each of which are covalently linked in a variety of ways to a nitric oxide group. Specific examples include angiotensin receptor blockers with one covalently-linked nitric oxide group, and angiotensin receptor blockers with two independently-covalently-linked nitric oxide groups. WO2005023182 describes nitrosated and nitrosylated cardiovascular compounds, and compositions comprising at least one nitrosated and nitrosylated cardiovascular compound and optionally at least one nitric oxide donor. The cardiovascular compound which is nitrosated or nitrosylated may be an aldosterone antagonist, an angiotensin II receptor antagonist, a calcium channel blocker, an endothelin antagonist, a hydralazine compound, a neutral endopeptidase inhibitor or a renin inhibitor. The nitric oxide donor may be selected from S-nitrosothiols, nitrites, nitrates, N-oxo-N-nitrosamines, furoxans, and sydnonimines.

WO2005070868 describes combination therapy for treating cyclooxygenase-2 mediated diseases or conditions at risk of thrombotic cardiovascular events which involves administering selected cyclooxygenase-2 inhibitor in combination with a nitric oxide donating compound such as 5,6-bis(nitrooxy)hexyl acetate, 6-hydroxyhexane-1,2-diyl dinitrate, 5-hydroxypentane-1,2-diyl dinitrate, (5R)-5,6-bis(nitrooxy)hexyl 4-nitrobenzoate, (5S)-5,6-bis(nitrooxy)hexyl 4-nitrobenzoate, (2R)-6-hydroxyhexane-1,2-diyl dinitrate, (2S)-6-hydroxyhexane-1,2-diyl dinitrate, (2S)-propane-1,2-diyl dinitrate, and (2R)-propane-1,2-diyl dinitrate.

SUMMARY OF THE INVENTION

The present invention includes angiotensin II receptor antagonist nitrooxy derivatives, including 2-butyl-4-chloro-1-[(2'-(1-H-tetrazol-5-yl)biphenyl-4-yl)methyl]-imidazole-5-carboxylate nitrooxy derivatives, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist derivatives having the general formula:

$$R-Y \atop [Y]_{0-1} \qquad (I)$$

wherein R is selected from the group consisting of

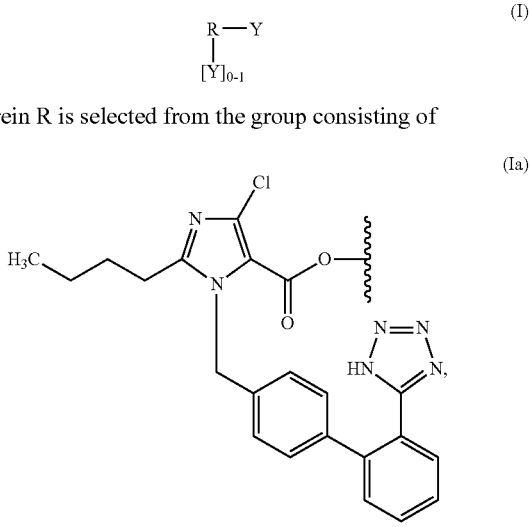

(Ia)

(Ib)
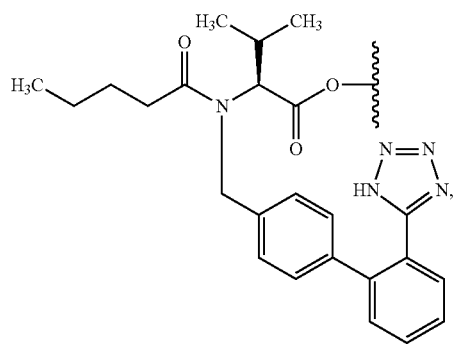
(Ic)
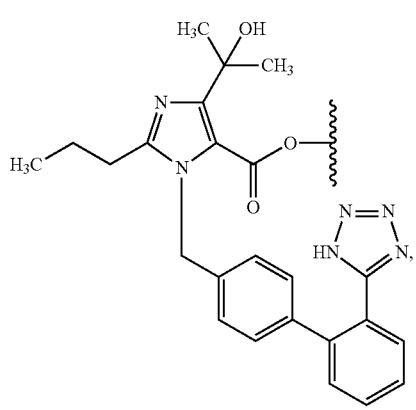
(Id)
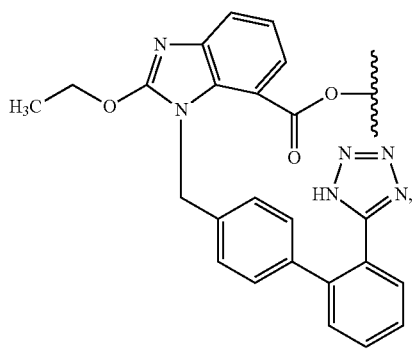
(Ie)
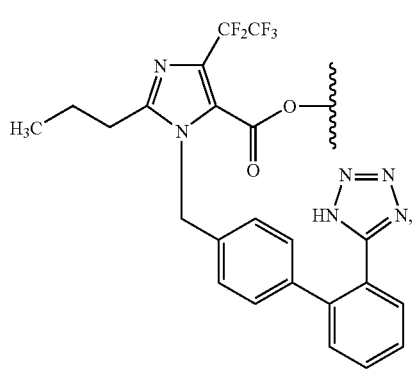
(If)
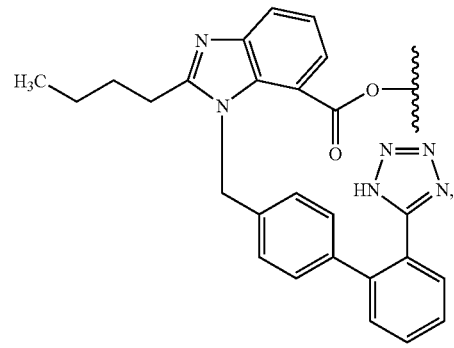
(Ig)
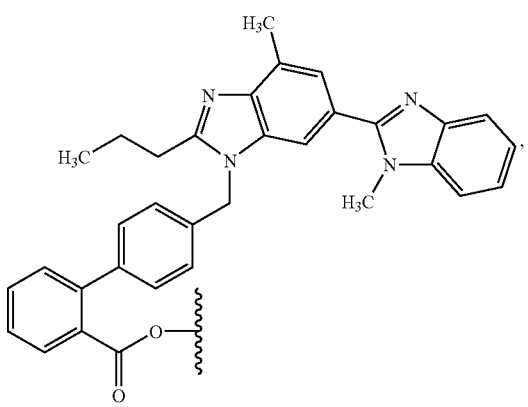
(Ih)
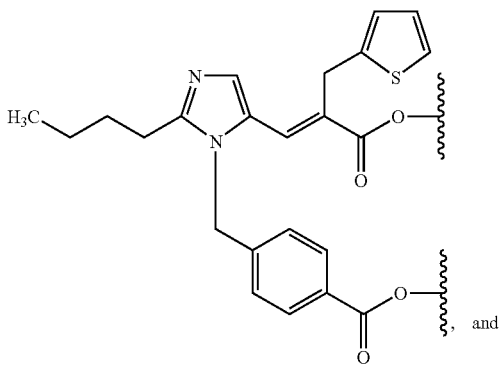
, and
(Ii)
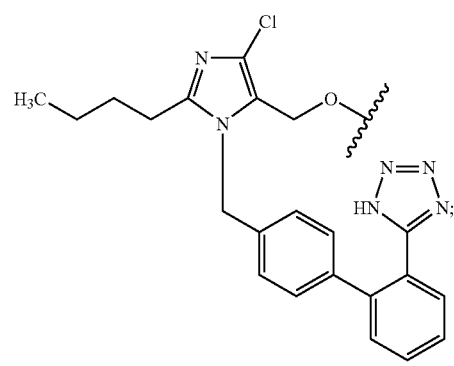

Y is selected from the group consisting of

1) 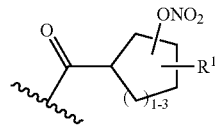

2) 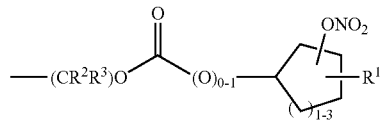

provided that when Y is

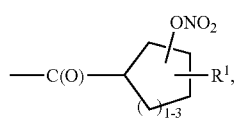

then R is

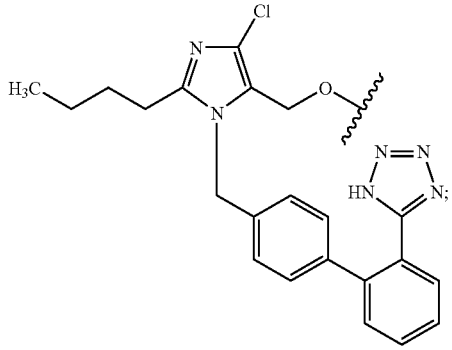

R¹ is selected from the group consisting of
—O—$C_{1-6}$ alkyl,
—O-aryl,
—O-heteroaryl,
—O—$C_{3-8}$ cycloalkyl,
—$C_{1-6}$ alkyl,
-aryl,
-heteroaryl, and
—$C_{3-8}$ cycloalkyl;

R² and R³ are independently selected from the group consisting of hydrogen and $C_{1-4}$ alkyl, or a pharmaceutically acceptable salt thereof.

In one embodiment of the invention, R is (Id)

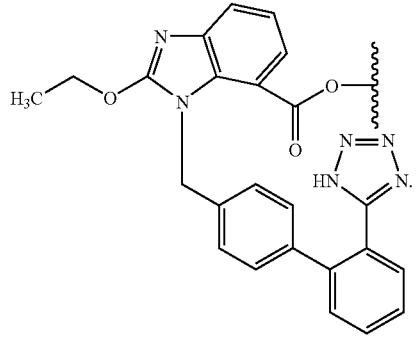

In another embodiment of the invention, R is (Ic)

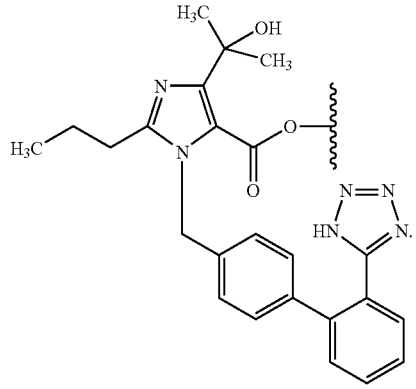

In another embodiment of the invention, R is (Ib)

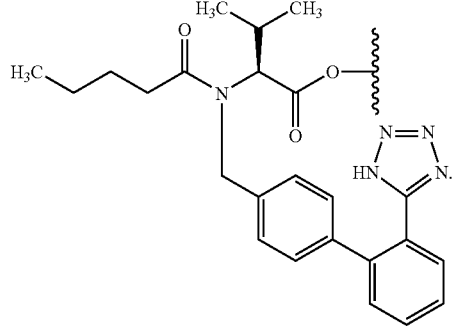

In another embodiment of the invention, R is (Ig)

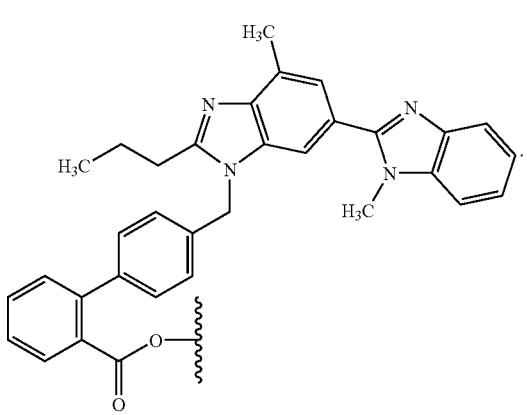

In another embodiment of the invention, R is

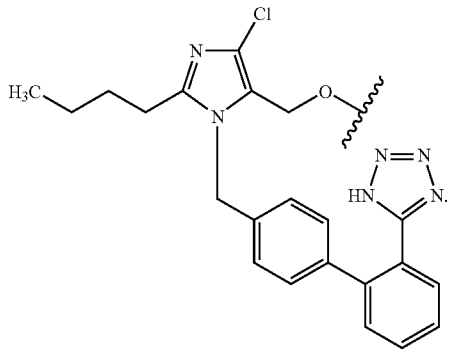
(Ii)

In another embodiment of the invention, R is

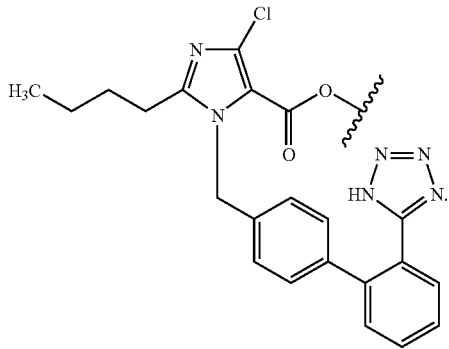
(Ia)

In another embodiment of the invention, $R^1$ is —O—$C_{1-6}$ alkyl.

In another embodiment of the invention, $R^1$ is —$OCH_3$.

In another embodiment of the invention, $R^2$ is hydrogen and $R^3$ is $C_{1-4}$ alkyl.

In another embodiment of the invention, $R^2$ is hydrogen and $R^3$ is $CH_3$.

In another embodiment of the invention, Y is

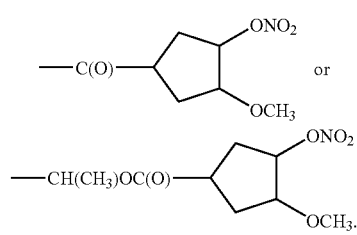

In another embodiment of the invention, Y is

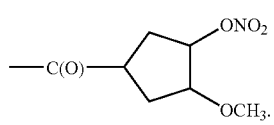

In another embodiment of the invention, Y is

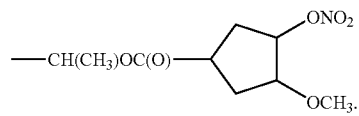

In another embodiment of the invention, Y is selected from the group consisting of

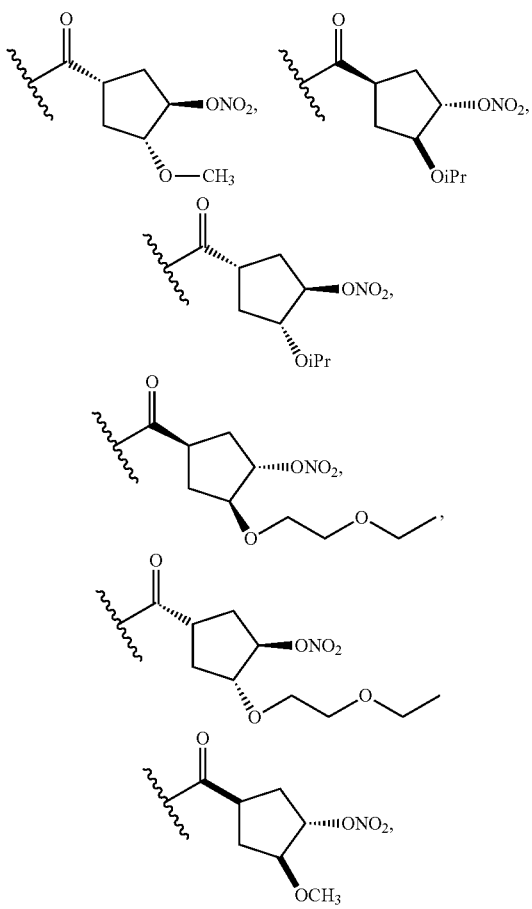

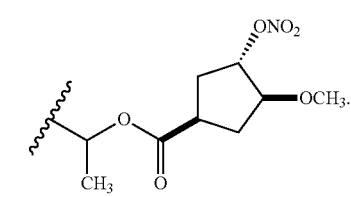

In another embodiment of the invention, Y is selected from the group consisting of
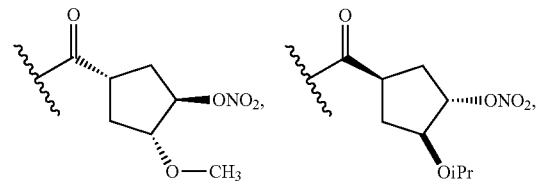
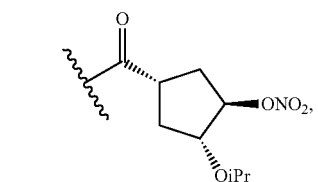
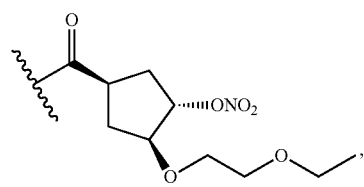
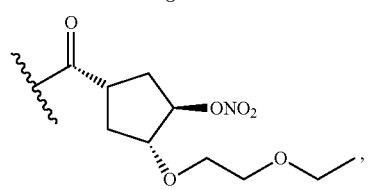
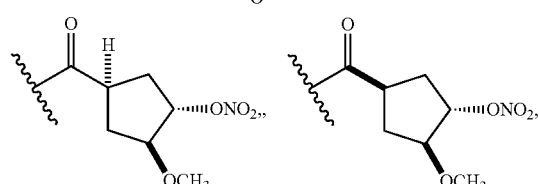
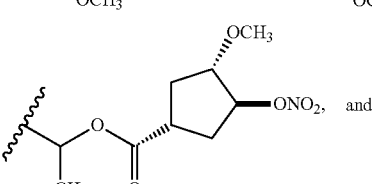
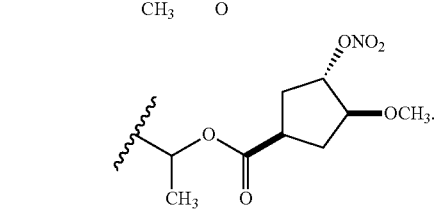 and
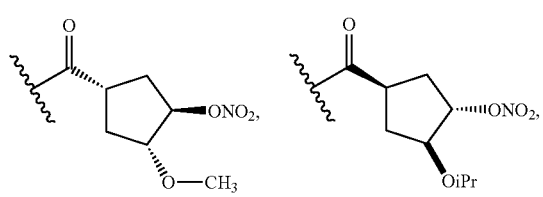
In another embodiment of the invention, Y is selected from the group consisting of
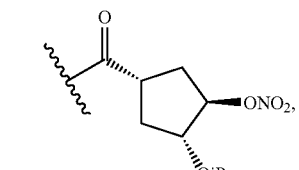
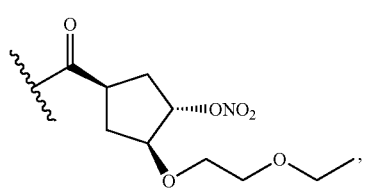
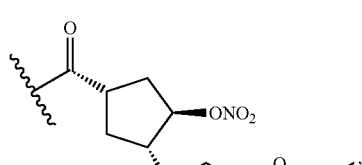
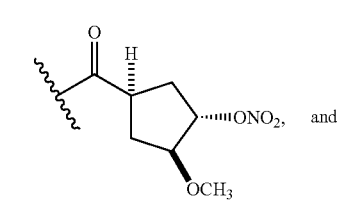
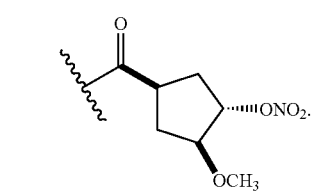 and
In another embodiment of the invention, Y is selected from the group consisting of
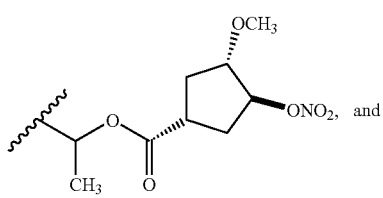 and
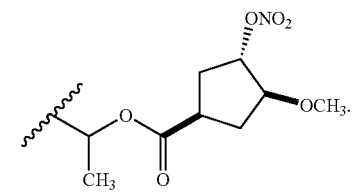

In another embodiment of the invention, the compound is

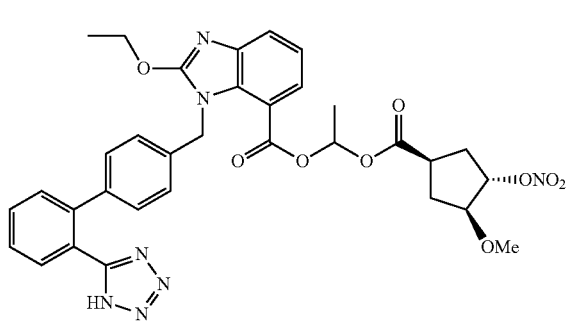

or a pharmaceutically acceptable salt thereof.

In another embodiment of the invention, the compound is

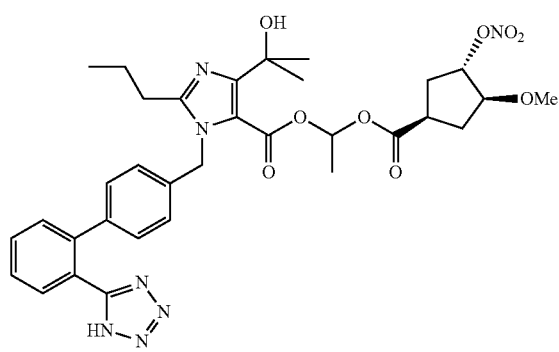

or a pharmaceutically acceptable salt thereof.

In another embodiment of the invention, the compound is

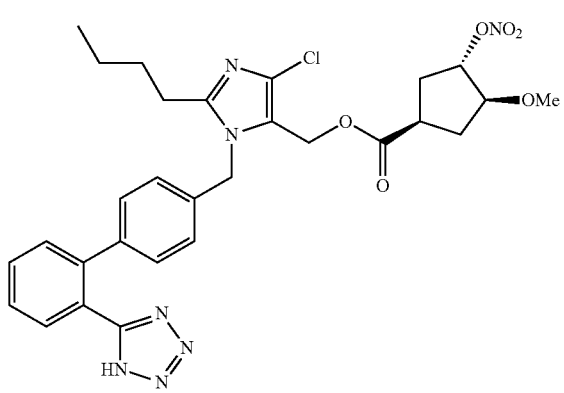

or a pharmaceutically acceptable salt thereof.

In another embodiment of the invention, the compound is

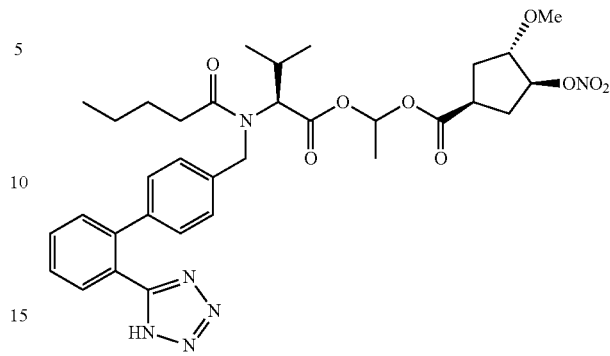

or a pharmaceutically acceptable salt thereof.

In another embodiment of the invention, the compound is

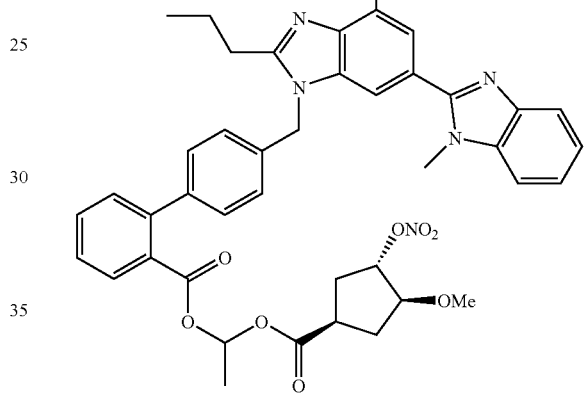

or a pharmaceutically acceptable salt thereof.

In another embodiment of the invention, the compound is selected from the group consisting of
(2-butyl-4-chloro-1-{[2'-(1H-tetrazol-5-yl)biphenyl-4-yl]methyl}-1H-imidazol-5-yl)methyl (1R,3S,4S)-3-methoxy-4-(nitrooxy)cyclopentanecarboxylate,
1-({[(1R,3S,4S)-3-methoxy-4-(nitrooxy)cyclopentyl]carbonyl}oxy)ethyl 2-ethoxy-1-{[2'-(1H-tetrazol-5-yl)biphenyl-4-yl]methyl}-1H-benzimidazole-7-carboxylate,
1-({[(1R,3S,4S)-3-methoxy-4-(nitrooxy)cyclopentyl]carbonyl}oxy)ethyl 4-(2-hydroxypropan-2-yl)-2-propyl-1-{[2'-(1H-tetrazol-5-yl)biphenyl-4-yl]methyl}-1H-imidazole-5-carboxylate,
(1R)-1-({[(1R,3S,4S)-3-methoxy-4-(nitrooxy)cyclopentyl]carbonyl}oxy)ethyl N-pentanoyl-N-{[2'-(1H-tetrazol-5-yl)biphenyl-4-yl]methyl}-L-valinate,
(1S)-1-({[(1R,3S,4S)-3-methoxy-4-(nitrooxy)cyclopentyl]carbonyl}oxy)ethyl N-pentanoyl-N-{[2'-(1H-tetrazol-5-yl)biphenyl-4-yl]methyl}-L-valinate,
1-({[(1R,3S,4S)-3-methoxy-4-(nitrooxy)cyclopentyl]carbonyl}oxy)ethyl 4'-[(1,7'-dimethyl-2'-propyl-1H,3'H-2,5'-bibenzimidazol-3'-yl)methyl]biphenyl-2-carboxylate,
(1R)-1-({[(1R,3S,4S)-3-methoxy-4-(nitrooxy)cyclopentyl]carbonyl}oxy)ethyl 2-butyl-4-chloro-1-{[2'-(1H-tetrazol-5-yl)biphenyl-4-yl]methyl}-1H-imidazole-5-carboxylate, and (1S)-1-({[(1R,3S,4S)-3-methoxy-4-(nitrooxy)cyclopentyl] carbonyl}oxy)ethyl 2-butyl-4-chloro-1-{[2'-(1H-tetrazol-5-yl)biphenyl-4-yl]methyl}-1H-imidazole-5-carboxylate, or a pharmaceutically acceptable salt thereof.

The compounds of the present invention may have one or more chiral centers, providing for up to two ((R) and (S)) or four (R,R), (S,S), (R,S), and (S,R) stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. The structure marking "*" indicates the location of a carbon atom that is a chiral center. Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. ⸺ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The term "aryl", alone or in combination, relates to a phenyl, naphthyl or indanyl group, preferably a phenyl group. The abbreviation "Ph" represents phenyl.

Aryl groups may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $HS(O)_{0-2}$—, ($C_1$-$C_6$ alkyl)$S(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_1$-$C_6$ alkyl)$S(O)_{0-2}$, ($C_1$-$C_6$ alkyl)$C(O)NH$—, $HC(O)NH$—, $H_2N$—$C(NH)$—, —$O(C_1$-$C_6$ alkyl)$CF_3$, ($C_1$-$C_6$ alkyl)$C(O)$—, $HC(O)$—, ($C_1$-$C_6$ alkyl)$OC(O)$—, $HOC(O)$—, ($C_1$-$C_6$ alkyl)$O(C_1$-$C_6$ alkyl)-, $HO(C_1$-$C_6$ alkyl)-, ($C_1$-$C_6$ alkyl)$C(O)_{1-2}$($C_1$-$C_6$ alkyl)-, ($C_1$-$C_6$ alkyl)$C(O)_{1-2}$—, $HC(O)_{1-2}$($C_1$-$C_6$ alkyl)-, ($C_1$-$C_6$ alkyl)$OC(O)NH$—, $HOC(O)NH$—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "heteroaryl", alone or in combination, means a 5 or 6-membered aromatic ring containing 1, 2, 3 or 4 heteroatoms independently selected from N, O or S, e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

Heteroaryl groups may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0-2}$—, $HS(O)_{0-2}$—, ($C_1$-$C_6$ alkyl)$S(O)(O)_2$($C_1$-$C_6$ alkyl)-, $HS(O)_{0-2}$($C_1$-$C_6$ alkyl)-, ($C_1$-$C_6$ alkyl)$S(O)_{0-2}$—, ($C_1$-$C_6$ alkyl)$C(O)NH$—, $HC(O)NH$—, $H_2N$—$C(NH)$—, —$O(C_1$-$C_6$ alkyl)$CF_3$, $HC(O)$—, ($C_1$-$C_6$ alkyl)$C(O)$—, ($C_1$-$C_6$ alkyl)$OC(O)$—, $HOC(O)$—, ($C_1$-$C_6$ alkyl)$O(C_1$-$C_6$ alkyl)-, $HO(C_1$-$C_6$ alkyl)-, ($C_1$-$C_6$ alkyl)$O$—, ($C_1$-$C_6$ alkyl)$C(O)_{1-2}$($C_1$-$C_6$ alkyl)-, $HC(O)_{1-2}$($C_1$-$C_6$ alkyl)-, ($C_1$-$C_6$ alkyl)$C(O)_{1-2}$, ($C_1$-$C_6$ alkyl)$OC(O)NH$—, $HOC(O)NH$—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —$C(O)C_{1-6}$ alkyl, —$C(O)NHC_1$-$C_6$ alkyl, —$C(O)NH_2$, —$C_1$-$C_6$ alkyl$C(O)NH_2$, —$C_1$-$C_6$ alkyl$OC(O)NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

The term "cycloalkyl", alone or in combination with other groups, unless indicated otherwise, means a saturated cyclic hydrocarbon ring system with 3 to 8 carbon atoms, e.g., cyclopropyl, cyclobutyl, cyclopentyl, cyclohexyl, cycloheptyl and cyclooctyl. This may be represented by "$C_{3-8}$ cycloalkyl" or "$C_3$-$C_8$ cycloalkyl"). When the intended meaning is other than this, for example, when the number of carbon atoms is in the range of three to six carbon atoms, this meaning is represented in like fashion as "$C_{3-6}$ cycloalkyl" or "$C_3$-$C_6$ cycloalkyl". Cycloalkyl groups may be unsubstituted, or substituted with 1-3 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, where such substitution results in formation of a stable compound.

Intermediate 1

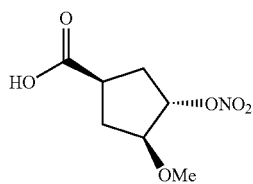

(1R,3S,4S)-3-methoxy-4-(nitrooxy)cyclopentanecarboxylic acid

Step A: methyl (1R,3s,5S)-6-oxabicyclo[3.1.0]hexane-3-carboxylate

To a solution of methyl cyclopent-3-ene-1-carboxylate (5.05 g, 40.0 mmol) in dichloromethane (400 mL) at 0° C. was added 3-chloroperbenzoic acid (10.6 g, 46.0 mmol) portionwise. The reaction was stirred for 12 hours at room temperature. The reaction mixture was concentrated and diluted with diethyl ether (300 mL). The organic layer was washed with water, aqueous potassium carbonate, and brine. It was dried (sodium sulfate), and chromatography on silica gel, eluting with 10/90→30/70 ethyl acetate/hexanes, afforded the title compound as a colorless liquid. $^1$H NMR (500 MHz, CDCl$_3$) δ 1.90 (dd, J=9.0, 14.0 Hz, 2H), 2.36 (dd, J=9.0, 14.0 Hz, 2H), 2.66 (quintet, J=9.0 Hz, 1H), 3.53 (s, 2H), 3.68 (s, 3H).

Step B: methyl (1R*,3R*,4R*)-3-hydroxy-4-methoxycyclopentanecarboxylate

To a solution of methyl (1R,3s,5S)-6-oxabicyclo[3.1.0]hexane-3-carboxylate (7.10 g, 49.9 mmol) in methanol (50 mL) was added concentrated sulfuric acid (0.023 mL, 0.43 mmol), and the solution was allowed to stir at room temperature. After 4 hours, the reaction mixture was concentrated in vacuo, and chromatography on silica gel, eluting with 20/80→100/0 ethyl acetate/hexanes, afforded the title compound as a colorless liquid. $^1$H NMR (500 MHz, CDCl$_3$) δ 1.84-1.91 (m, 2H), 2.23 (ddd, J=6.1, 8.0, 13.9 Hz, 1H), 2.33 (ddd, J=6.2, 9.1, 13.7 Hz, 1H), 3.03 (quintet, J=8.5 Hz, 1H), 3.35 (s, 3H), 3.61 (dt, J=3.5, 5.9 Hz, 1H), 3.69 (s, 3H), 4.21 (td, J=3.6, 6.1 Hz, 1H).

Step C: methyl (1R*,3S*,4S*)-3-methoxy-4-(nitrooxy)cyclopentanecarboxylate

To an acetic anhydride (10 mL) solution of nitric acid (5.0 mL, 78 mmol) at 0° C. was added methyl (1R*,3R*,4R*)-3-hydroxy-4-methoxycyclopentanecarboxylate (1.0 g, 5.7 mmol). After 2 hours, the reaction mixture was slowly added to a saturated solution of sodium hydrogen carbonate solution. The aqueous layer was extracted with ethyl acetate (3×100 mL), and the combined organic extracts were washed with brine, dried (magnesium sulfate), and concentrated in vacuo to afford the crude product. The residue was purified by column chromatography on silica gel, eluting with 5/95→25/75 ethyl acetate/hexanes to afford the title compound as a colorless liquid. $^1$H NMR (500 MHz, CDCl$_3$) δ 1.98-2.10 (m, 2H), 2.36 (ddd, J=6.3, 8.7, 13.9 Hz, 1H), 2.51 (ddd, J=6.5, 8.9, 15.2 Hz, 1H), 2.97 (quintet, J=8.5 Hz, 1H), 3.37 (s, 3H), 3.71 (s, 3H), 3.80-3.85 (m, 1H), 5.28 (td, J=2.4, 6.5 Hz, 1H). Chromatography of the racemic mixture over Chiralcel OD column, eluting with isopropanol/heptane, afforded the separate enantiomers, with the (1S,3R,4R)-stereoisomer as the faster eluting peak and the (1R,3S,4S)-stereoisomer as the slower eluting peak.

Step D: (1R,3S,4S)-3-methoxy-4-(nitrooxy)cyclopentanecarboxylic acid

A solution of methyl (1R,3S,4S)-3-methoxy-4-(nitrooxy)cyclopentanecarboxylate (0.66 g, 3.0 mmol) in methanol (12 mL) was cooled to 0° C. To this solution was added 4N potassium hydroxide (1.5 mL, 6.0 mmol) dropwise over 10 minutes, and the solution was stirred and allowed to warm to 10° C. over 3 hours. The reaction mixture was acidified by the addition of concentrated hydrochloric acid and extracted with chloroform (3×15 mL). The combined organic layers were washed with brine and dried (sodium sulfate) to give the title compound as a colorless oil. $^1$H NMR (500 MHz, CDCl$_3$) δ 2.06-2.14 (m, 2H), 2.34 (ddd, J=6.2, 9.1, 14.1 Hz, 1H), 2.54 (ddd, J=6.6, 8.7, 15.0 Hz, 1H), 3.03 (quintet, J=8.4 Hz, 1H), 3.38 (s, 3H), 3.82-3.86 (m, 1H), 5.27-5.32 (m, 1H), 8.5-11.5 (br, 1H).

Intermediate 2

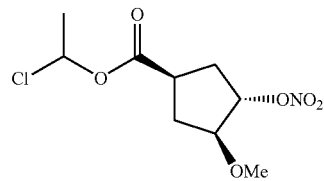

1-chloroethyl (1R,3S,4S)-3-methoxy-4-(nitrooxy)cyclopentanecarboxylate

To a d-chloroform (60 mL) solution of (1R,3S,4S)-3-methoxy-4-(nitrooxy)cyclopentane carboxylic acid (4.59 g, 22.4 mmol) was added oxalyl chloride (2.40 mL, 27.4 mmol), followed by a few drops of N,N-dimethylformamide. After 60 minutes, ¹H-NMR showed that the reaction was complete. To this reaction mixture was added zinc chloride (0.31 g, 2.27 mmol). The suspension was cooled to 0° C., and a d-chloroform solution (10 mL) of acetaldehyde (2.6 mL, 46.0 mmol) was slowly added to the reaction mixture over 5 minutes. The reaction was warmed up to room temperature and stirred for 17 hours. ¹H-NMR confirmed that the starting acid chloride has been consumed and most of the material was converted to the desired product. The reaction mixture was concentrated in vacuo, and chromatography of the residue over silica gel, eluting with 2/98→20/80 ethyl acetate/hexanes, afforded the title compound as a colorless liquid. ¹H NMR (500 MHz, CDCl₃) δ 1.80 (d, J=5.9 Hz, 3H), 2.04-2.14 (m, 2H), 2.28-2.36 (m, 1H), 2.50-2.60 (m, 1H), 3.01 (quintet, J=8.3 Hz, 1H), 3.37 (s, 3H), 3.81-3.85 (m, 1H), 5.26-5.31 (m, 1H), 6.54 (q, J=5.8 Hz, 1H, D1), 6.54 (q, J=5.9 Hz, 1H, D2).

Chromatography of the diasteromeric mixture over Chiralpak AD column, eluting with isopropanol/acetonitrile/carbon dioxide, afforded the separate disastereomers.

Intermediate 3, (1S)-1-chloroethyl (1R,3S,4S)-3-methoxy-4-(nitrooxy)cyclopentanecarboxylate: ¹H NMR (500 MHz, CDCl₃) δ 1.80 (d, J=5.8 Hz, 3H), 2.02-2.14 (m, 2H), 2.32 (ddd, J=6.1, 8.9, 14.0 Hz, 1H), 2.54 (ddd, J=6.5, 8.7, 15.0 Hz, 1H), 3.01 (quintet, J=8.3 Hz, 1H), 3.37 (s, 3H), 3.81-3.85 (m, 1H), 5.26-5.31 (m, 1H), 6.54 (q, J=5.8 Hz, 1H).

Intermediate 4, (1R)-1-chloroethyl (1R,3S,4S)-3-methoxy-4-(nitrooxy)cyclopentanecarboxylate: ¹H NMR (500 MHz, CDCl₃) δ 1.80 (d, J=5.8 Hz, 3H), 2.04-2.11 (m, 2H), 2.33 (ddd, J=6.0, 9.1, 14.1 Hz, 1H), 2.56 (ddd, J=6.5, 8.6, 15.0 Hz, 1H), 3.01 (quintet, J=8.2 Hz, 1H), 3.37 (s, 3H), 3.81-3.85 (m, 1H), 5.26-5.31 (m, 1H), 6.54 (q, J=5.8 Hz, 1H).

Example 1

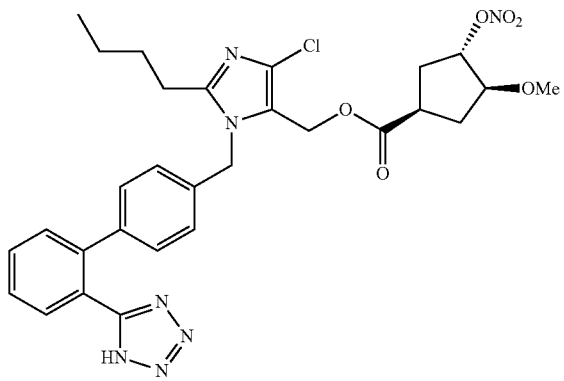

(2-butyl-4-chloro-1-{[2'-(1H-tetrazol-5-yl)biphenyl-4-yl]methyl}-1H-imidazol-5-yl)methyl (1R,3S,4S)-3-methoxy-4-(nitrooxy)cyclopentanecarboxylate A mixture of potassium losartan (974 mg, 2.11 mmol), (1R,3S,4S)-3-methoxy-4-(nitrooxy)cyclopentanecarboxylic acid (intermediate 1, 429 mg, 2.09 mmol), 1-ethyl-3-(3-dimethylaminopropyl)carbodiimide hydrochloride (447 mg, 2.33 mmol), and N-methylmorpholine (0.50 mL, 4.6 mmol) was dissolved in dichloromethane (20 mL) and stirred for 2 days with catalytic amounts of 4-(dimethylamino)pyridine. ¹H NMR (500 MHz, CDCl₃) δ 0.84 (t, J=7.3 Hz, 3H), 1.28 (sextet, J=7.3 Hz, 2H), 1.56 (quintet, J=7.3 Hz, 2H), 1.78-1.84 (m, 1H), 1.88-1.92 (m, 1H), 2.08-2.15 (m, 1H), 2.30-2.36 (m, 1H), 2.38 (t, J=6.7 Hz, 2H), 2.71 (quintet, J=8.2 Hz, 1H), 3.26 (s, 3H), 3.70-3.75 (m, 1H), 4.87 (d, J=13.9 Hz, 1H), 4.91 (d, J=13.7 Hz, 1H), 5.13 (s, 2H), 5.15-5.19 (m, 1H), 6.77 (d, J=8.0 Hz, 2H), 7.10 (d, J=8.2 Hz, 2H), 7.41 (d, J=7.8 Hz, 1H), 7.52 (td, J=1.4, 7.6 Hz, 1H), 7.61 (td, J=1.4, 7.6 Hz, 1H), 7.84 (dd, J=0.9, 7.7 Hz, 1H); LC-MS: m/z 610.4 (M+H).

Example 2

1-({[(1R,3S,4S)-3-methoxy-4-(nitrooxy)cyclopentyl]carbonyl}oxy)ethyl 2-ethoxy-1-{[2'-(1H-tetrazol-5-yl)biphenyl-4-yl]methyl}-1H-benzimidazole-7-carboxylate Step A: 1-({[(1R,3S,4S)-3-methoxy-4-(nitrooxy)cyclopentyl]carbonyl}oxy)ethyl 2-ethoxy-1-{[2'-(1-trityl-1H-tetrazol-5-yl)biphenyl-4-yl]methyl}-1H-benzimidazole-7-carboxylate A mixture of 2-ethoxy-1-{[2'-(1-trityl-1H-tetrazol-5-yl)biphenyl-4-yl]methyl}-1H-benzimidazole-7-carboxylic acid (2180 mg, 3.19 mmol), cesium carbonate (2150 mg, 6.60 mmol), and tetrabutylammonium hydrogen sulfate (538 mg, 1.59 mmol) was charged with a N,N-dimethylformamide (10 mL) solution of 1-chloroethyl (1R,3S,4S)-3-methoxy-4-(nitrooxy)cyclopentanecarboxylate (intermediate 2, 834 mg, 3.11 mmol). The reaction mixture was heated at 40° C. for 16 hours, and the reaction mixture was purified by column chromatography, eluting with 10/90→70/30 ethyl acetate/hexanes to give the title compound as a white solid. ¹H NMR (500 MHz, CDCl₃) δ 1.36 (d, J=5.5 Hz, 3H, D1), 1.36 (d, J=5.5 Hz, 3H, D2), 1.41 (t, J=7.1 Hz, 3H), 1.94-2.05 (m, 2H), 2.19-2.27 (m, 1H), 2.46-2.54 (m, 1H), 2.76-2.87 (m, 1H), 3.30 (s, 3H, D1), 3.30 (s, 3H, D2), 3.76 (q, J=4.1 Hz, 1H), 4.61 (q, J=7.1 Hz, 2H, D1), 4.61 (q, J=7.1 Hz, 2H, D2), 5.23 (t, J=6.0 Hz, 1H), 5.53 (d, J=16.0 Hz, 1H), 5.58 (d, J=16.0 Hz, 1H), 6.75 (d, J=6.9 Hz, 2H), 6.88-6.95 (m, 7H), 6.98 (d, J=8.0 Hz, 2H), 7.17 (dt, J=2.0, 7.8 Hz, 1H), 7.23 (t, J=7.7 Hz, 6H), 7.26-7.34 (m, 4H), 7.40-7.48 (m, 2H), 7.54 (dd, J=1.1, 8.0 Hz, 1H), 7.76 (d, J=7.7 Hz, 1H), 7.86 (d, J=7.8 Hz, 1H); LC-MS: m/z 913.6 (M+H).

Step B: 1-({[(1R,3S,4S)-3-methoxy-4-(nitrooxy)cyclopentyl]carbonyl}oxy)ethyl 2-ethoxy-1-{[2'-(1H-tetrazol-5-yl)biphenyl-4-yl]methyl}-1H-benzimidazole-7-carboxylate A methanol (20 mL) solution of 1-({[(1R,3S,4S)-3-methoxy-4-(nitrooxy)cyclopentyl]carbonyl}oxy)ethyl 2-ethoxy- 1-{[2'-(1-trityl-1H-tetrazol-5-yl)biphenyl-4-yl]methyl}-1H-benzimidazole-7-carboxylate (1420 mg, 1.62 mmol) was heated to 70° C. for 2 hours. The reaction mixture was concentrated in vacuo, and the residue was purified by column chromatography, eluting with 0/100→10/90 methanol/dichloromethane to give the title compound as a white solid. Chromatography of the diasteromeric mixture over Chiralpak IC column, eluting with methanol/carbon dioxide, afforded the separate disastereomers D1 and D2.

D1: $^1$H NMR (500 MHz, CD$_3$CN) δ 1.38 (d, J=5.7 Hz, 3H), 1.39 (t, J=7.2 Hz, 3H), 1.89-1.95 (m, 1H), 2.00 (ddd, J=2.4, 8.5, 14.9 Hz, 1H), 2.23 (ddd, J=6.2, 9.0, 13.9 Hz, 1H), 2.41 (ddd, J=7.1, 7.8, 15.0 Hz, 1H), 2.95 (quintet, J=8.3 Hz, 1H), 3.26 (s, 3H), 3.79-3.84 (m, 1H), 4.49 (qd, J=7.2, 10.3 Hz, 1H), 4.54 (qd, J=7.2, 10.4 Hz, 1H), 5.19-5.23 (m, 1H), 5.51 (d, J=16.5 Hz, 1H), 5.57 (d, J=16.6 Hz, 1H), 6.89 (d, J=8.4 Hz, 2H), 6.90 (q, J=5.4 Hz, 1H), 6.97 (d, J=8.2 Hz, 2H), 7.13 (t, J=7.9 Hz, 1H), 7.42 (d, J=7.8 Hz, 1H), 7.49-7.55 (m, 3H), 7.60 (dt, J=1.2, 7.6 Hz, 1H), 7.70 (d, J=7.7 Hz, 1H); LC-MS: m/z 672.4 (M+H).

D2: $^1$H NMR (500 MHz, CD$_3$CN) δ 1.38 (d, J=5.7 Hz, 3H), 1.39 (t, J=6.9 Hz, 3H), 1.89 (ddd, J=4.8, 7.2, 13.9 Hz, 1H), 2.02 (ddd, J=2.5, 8.5, 15.0 Hz, 1H), 2.23 (ddd, J=6.1, 9.1, 13.9 Hz, 1H), 2.43 (ddd, J=6.9, 8.3, 15.0 Hz, 1H), 2.97 (quintet, J=8.3 Hz, 1H), 3.24 (s, 3H), 3.78-3.83 (m, 1H), 4.48 (qd, J=7.0, 10.3 Hz, 1H), 4.54 (qd, J=7.1, 10.3 Hz, 1H), 5.23 (td, J=2.6, 6.7 Hz, 1H), 5.52 (d, J=16.5 Hz, 1H), 5.58 (d, J=16.4 Hz, 1H), 6.90 (q, J=5.4 Hz, 1H), 6.90 (d, J=8.2 Hz, 2H), 6.98 (d, J=8.3 Hz, 2H), 7.13 (t, J=7.9 Hz, 1H), 7.42 (dd, J=1.1, 7.8 Hz, 1H), 7.48-7.56 (m, 3H), 7.61 (dt, J=1.4, 7.6 Hz, 1H), 7.70 (dd, J=1.3, 7.6 Hz, 1H); LC-MS: m/z 672.4 (M+H).

Example 3

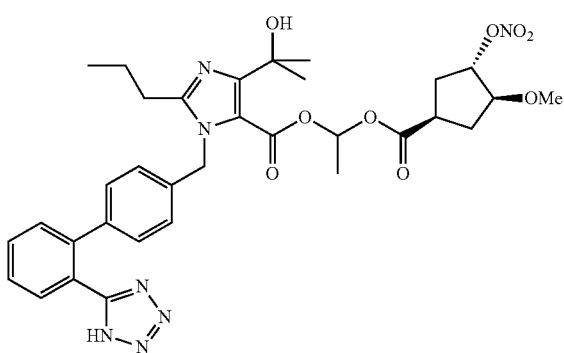

1-({[1(1R,3S,4S)-3-methoxy-4-(nitrooxy)cyclopentyl]carbonyl}oxy)ethyl 4-(2-hydroxypropan-2-yl)-2-propyl-1-{[2'-(1H-tetrazol-5-yl)biphenyl-4-yl]methyl}-1H-imidazole-5-carboxylate The title compound was prepared by following the procedure for example 2, except that the reagent 2-ethoxy-1-{[2'-(1-trityl-1H-tetrazol-5-yl)biphenyl-4-yl]methyl}-1H-benzimidazole-7-carboxylic acid was replaced by 4-(2-hydroxypropan-2-yl)-2-propyl-1-{[2'-(1-trityl-1H-tetrazol-5-yl)biphenyl-4-yl]methyl}-1H-imidazole-5-carboxylic acid. $^1$H NMR (500 MHz, CDCl$_3$) δ 0.96 (t, J=7.3 Hz, 3H), 1.44 (d, J=5.0 Hz, 3H, D1), 1.46 (d, J=5.0 Hz, 3H, D2), 1.57 (s, 6H), 1.73 (sextet, J=7.8 Hz, 2H), 1.82-2.02 (m, 2H), 2.18-2.26 (m, 1H), 2.31-2.40 (m, 1H), 2.58 (t, J=7.9 Hz, 2H), 2.90 (quintet, J=7.8 Hz, 1H, D1), 2.90 (quintet, J=7.8 Hz, 1H, D2), 3.24 (s, 3H, D1), 3.24 (s, 3H, D2), 3.56-3.72 (m, 1H), 5.14-5.20 (m, 1H), 5.41 (d, J=16.6 Hz, 1H, D1), 5.41 (d, J=16.6 Hz, 1H, D2), 5.48 (d, J=16.8 Hz, 1H, D1), 5.48 (d, J=16.8 Hz, 1H, D2), 6.87 (d, J=8.2 Hz, 2H), 6.93 (q, J=5.4 Hz, 1H, D1), 6.93 (q, J=5.4 Hz, 1H, D2), 7.15 (dd, J=2.0, 8.2 Hz, 2H), 7.43 (d, J=7.5 Hz, 1H), 7.55 (dt, J=1.4, 7.6 Hz, 1H), 7.61 (dt, J=7.5, 1.3 Hz, 1H), 8.01 (dd, J=1.3, 7.7 Hz, 1H); LC-MS: m/z 678.3 (M+H).

Example 4

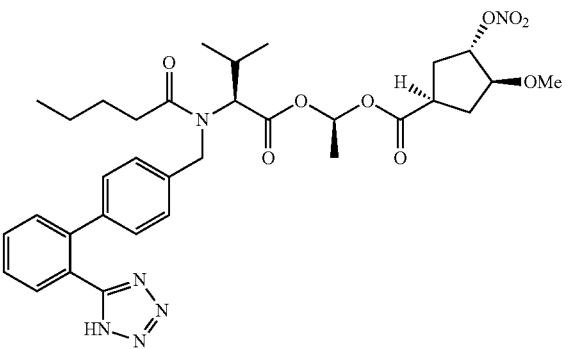

(1R)-1-({[(1R,3S,4S)-3-methoxy-4-(nitrooxy)cyclopentyl]carbonyl}oxy)ethyl N-pentanoyl-N-{[2'-(1H-tetrazol-5-yl)biphenyl-4-yl]methyl}-L-valinate The title compound was prepared by following the procedure for example 2, except that the reagent 2-ethoxy-1-{[2'-(1-trityl-1H-tetrazol-5-yl)biphenyl-4-yl]methyl}-1H-benzimidazole-7-carboxylic acid was replaced by N-pentanoyl-N-{[2'-(1-trityl-1H-tetrazol-5-yl)biphenyl-4-yl]methyl}-L-valine and 1-chloroethyl (1R,3S,4S)-3-methoxy-4-(nitrooxy)cyclopentanecarboxylate (intermediate 2) was replaced by (1S)-1-chloroethyl (1R,3S,4S)-3-methoxy-4-(nitrooxy)cyclopentanecarboxylate (intermediate 3). LC-MS: m/z 667.3 (M+H).

Example 5

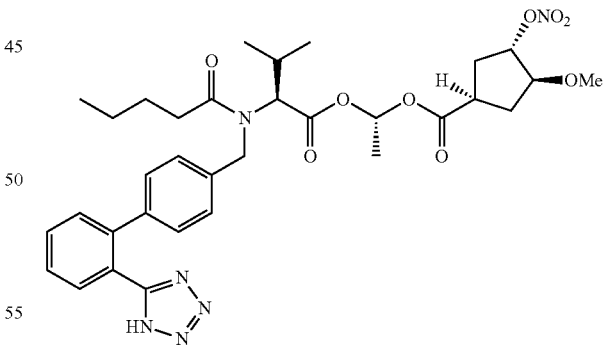

(1S)-1-({[(1R,3S,4S)-3-methoxy-4-(nitrooxy)cyclopentyl]carbonyl}oxy)ethyl N-pentanoyl-N-{[2'-(1H-tetrazol-5-yl)biphenyl-4-yl]methyl}-L-valinate The title compound was prepared by following the procedure for example 4, except that the reagent (1S)-1-chloroethyl (1R,3S,4S)-3-methoxy-4-(nitrooxy)cyclopentanecarboxylate (intermediate 3) was replaced by (1R)-1-chloroethyl (1R,3S,4S)-3-methoxy-4-(nitrooxy)cyclopentanecarboxylate (intermediate 4). LC-MS: m/z 667.3 (M+H).

Example 6

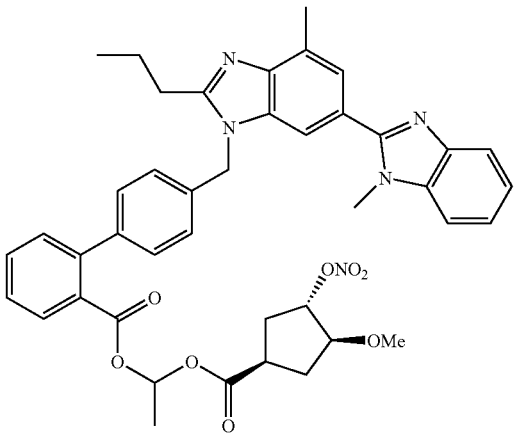

1-({[(1R,3S,4S)-3-methoxy-4-(nitrooxy)cyclopentyl]carbonyl}oxy)ethyl 4'-[(1,7'-dimethyl-2'-propyl-1H,3'H-2,5'-bibenzimidazol-3'-yl)methyl]biphenyl-2-carboxylate The title compound was prepared by following the procedure for step A, example 2, except that the reagent 2-ethoxy-1-{[2'-(1-trityl-1H-tetrazol-5-yl)biphenyl-4-yl]methyl}-1H-benzimidazole-7-carboxylic acid was replaced by 4'-[(1,7'-dimethyl-2'-propyl-1H,3'H-2,5'-bibenzimidazol-3'-yl)methyl]biphenyl-2-carboxylic acid. $^1$H NMR (500 MHz, CDCl$_3$) δ 1.06 (t, J=7.4 Hz, 3H), 1.19 (d, J=5.5 Hz, 3H, D1), 1.19 (d, J=5.5 Hz, 3H, D2), 1.89 (sextet, J=7.6 Hz, 2H), 1.92-2.00 (m, 2H), 2.16-2.24 (m, 1H), 2.39-2.46 (m, 1H), 2.77 (s, 3H), 2.82-2.90 (m, 1H), 2.94 (t, J=8.0 Hz, 2H), 3.29 (s, 3H, D1), 3.29 (s, 3H, D2), 3.73-3.77 (m, 1H), 3.81 (s, 3H), 5.19-5.23 (m, 1H), 5.45 (s, 2H), 6.79 (q, J=5.5 Hz, 1H, D1), 6.79 (q, J=5.5 Hz, 1H, D2), 7.09 (d, J=8.2 Hz, 2H), 7.24 (d, J=7.7 Hz, 2H), 7.26-7.31 (m, 3H), 7.35-7.43 (m, 2H), 7.44 (s, 1H), 7.49 (s, 1H), 7.52 (dt, J=1.1, 7.6 Hz, 1H), 7.78-7.81 (m, 1H), 7.83 (dd, J=3.0, 7.7 Hz, 1H); LC-MS: m/z 746.4 (M+H).

Example 7

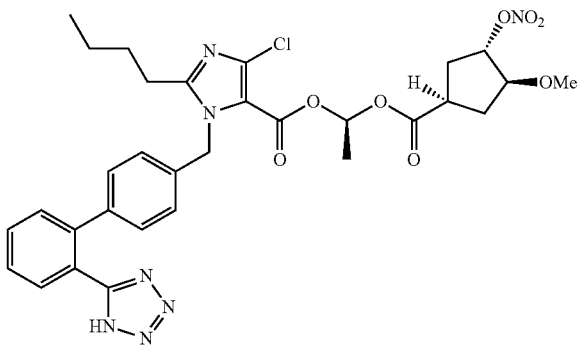

(1R)-1-({[[1R,3S,4S]-3-methoxy-4-(nitrooxy)cyclopentyl]carbonyl}oxy)ethyl 2-butyl-4-chloro-1-{[2'-(1H-tetrazol-5-yl)biphenyl-4-yl]methyl}-1H-imidazole-5-carboxylate The title compound was prepared by following the procedure for example 2, except that the reagent 2-ethoxy-1-{[2'-(1-trityl-1H-tetrazol-5-yl)biphenyl-4-yl]methyl}-1H-benzimidazole-7-carboxylic acid was replaced by 2-butyl-4-chloro-1-{[2'-(1-trityl-1H-tetrazol-5-yl)biphenyl-4-yl]methyl}-1H-imidazole-5-carboxylic acid and 1-chloroethyl (1R,3S,4S)-3-methoxy-4-(nitrooxy)cyclopentanecarboxylate (intermediate 2) was replaced by (1S)-1-chloroethyl (1R,3S,4S)-3-methoxy-4-(nitrooxy)cyclopentanecarboxylate (intermediate 3). $^1$H NMR (500 MHz, CDCl$_3$) δ 0.89 (t, J=7.4 Hz, 3H), 1.36 (sextet, J=7.4 Hz, 2H), 1.56 (d, J=5.4 Hz, 3H), 1.67 (quintet, J=7.7 Hz, 2H), 1.92-2.02 (m, 2H), 2.20-2.28 (m, 1H), 2.34-2.42 (m, 1H), 2.63 (t, J=7.4 Hz, 2H), 2.94 (quintet, J=8.2 Hz, 1H), 3.26 (s, 3H), 3.73-3.78 (m, 1H), 5.14-5.18 (m, 1H), 5.47 (d, J=16.5 Hz, 1H), 5.53 (d, J=16.4 Hz, 1H), 6.93 (d, J=8.1 Hz, 2H), 6.94 (q, J=5.4 Hz, 1H), 7.14 (d, J=8.3 Hz, 2H), 7.43 (d, J=7.2 Hz, 1H), 7.53 (dt, J=0.9, 7.6 Hz, 1H), 7.60 (dt, J=1.1, 7.5 Hz, 1H), 7.98 (d, J=7.7 Hz, 1H); LC-MS: m/z 668.1 (M+H).

Example 8

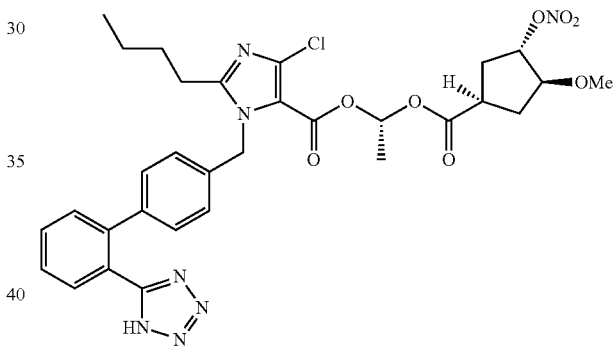

(1S)-1-({[[1R,3S,4S]-3-methoxy-4-(nitrooxy)cyclopentyl]carbonyl}ethyl 2-butyl-4-chloro-1-{[2'-(1H-tetrazol-5-yl)biphenyl-4-yl]methyl}-1H-imidazole-5-carboxylate The title compound was prepared by following the procedure for example 7, except that (1S)-1-chloroethyl (1R,3S,4S)-3-methoxy-4-(nitrooxy)cyclopentanecarboxylate (intermediate 3) was replaced by (1R)-1-chloroethyl (1R,3S,4S)-3-methoxy-4-(nitrooxy)cyclopentanecarboxylate (intermediate 4). $^1$H NMR (500 MHz, CDCl$_3$) δ 0.89 (t, J=7.4 Hz, 3H), 1.36 (sextet, J=7.4 Hz, 2H), 1.56 (d, J=5.4 Hz, 3H), 1.67 (quintet, J=7.7 Hz, 2H), 1.85-1.92 (m, 1H), 1.96-2.03 (m, 1H), 2.20-2.28 (m, 1H), 2.34-2.42 (m, 1H), 2.63 (t, J=7.4 Hz, 2H), 2.94 (quintet, J=8.2 Hz, 1H), 3.24 (s, 3H), 3.73-3.78 (m, 1H), 5.16-5.20 (m, 1H), 5.45 (d, J=16.5 Hz, 1H), 5.55 (d, J=16.4 Hz, 1H), 6.93 (d, J=8.1 Hz, 2H), 6.95 (q, J=5.4 Hz, 1H), 7.14 (d, J=8.3 Hz, 2H), 7.43 (d, J=7.2 Hz, 1H), 7.53 (dt, J=0.9, 7.6 Hz, 1H), 7.60 (dt, J=1.1, 7.5 Hz, 1H), 7.96 (d, J=7.7 Hz, 1H); LC-MS: m/z 668.1 (M+H).

Several examples were studied for systolic blood pressure lowering when orally administered to conscious telemetered dogs at 3 mpk (see Data Table 1).

DATA TABLE 1

| | Approximate change in systolic blood pressure (mm Hg) | | |
|---|---|---|---|
| | 1-6 h | 6-12 h | 12-18 h |
| Example 2, D1 | −15 | −11 | −1 |
| Example 2, D2 | −19 | −12 | −5 |
| Example 5 | −8 | −2 | 8 |
| Example 7 | −9 | −1 | 2 |

Vessel Relaxation

The ability of the compounds to induce vasorelaxation was tested in vitro in isolated rabbit thoracic aorta preparations (Wanstall J. C. et al., Br. J. Pharmacol., 134:463-472, 2001). Male New Zealand rabbits were anaesthetized with thiopental-Na (50 mg/kg, iv), sacrificed by exsanguinations and then the thorax was opened and the aorta dissected. Aortic ring preparations (4 mm in length) were set up in physiological salt solution (PSS) at 37° C. in small organ chambers (5 ml). The composition of PSS was (mM): NaCl 130, NaHCO$_3$ 14.9, KH$_2$PO$_4$ 1.2, MgSO$_4$ 1.2, HEPES 10, CaCl$_2$, ascorbic acid 170 and glucose 1.1 (95% O$_2$/5% CO$_2$; pH 7.4). Each ring was mounted under 2 g passive tension. Isometric tension was recorded with a Grass transducer (Grass FT03) attached to a BIOPAC MP150 System. Preparations were allowed to equilibrate for 1 h, and then contracted submaximally with noradrenaline (NA, 1 µM) and, when the contraction was stable, acetylcholine (ACh, 10 µM) was added. A relaxant response to ACh indicated the presence of a functional endothelium. Vessels that were unable to contract NA or showed no relaxation to ACh were discarded. When a stable precontraction was reached, a cumulative concentration-response curve to either of the vasorelaxant agents was obtained in the presence of a functional endothelium. Each arterial ring was exposed to only one combination of inhibitor and vasorelaxant. Moreover, the effect of the soluble guanylyl cyclase inhibitor ODQ (1-H-(1,2,4)-oxadiazol(4,3-a)quinoxalin-1-one) on vasorelaxation elicited by the compounds was examined preincubating the aortic rings with ODQ (10 µM) for 20 min.

Example 2 was evaluated for vessel relaxation. In vitro, tissue-based measure of vessel relaxation, determined in rabbit aortic slices, demonstrated vessel relaxation according to the indicated EC$_{50}$ (molar concentration of compound which produces 50% of the maximum possible response for that compound—Data Table 2).

DATA TABLE 2

| | EC$_{50}$ in vessel relaxation assay |
|---|---|
| Example 2, D2 | >25 µM |

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

What is claimed is:

1. A compound which is

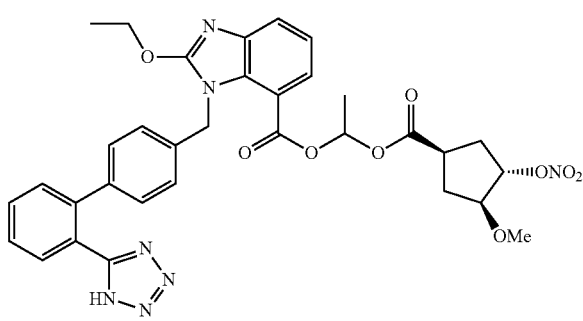

or a pharmaceutically acceptable salt thereof.

2. A pharmaceutical composition comprising a compound of claim 1 and a pharmaceutically acceptable carrier.

3. A pharmaceutical composition comprising a compound of claim 1, a diuretic, and a pharmaceutically acceptable carrier.

* * * * *